US008304596B2

(12) United States Patent
LaStella

(10) Patent No.: US 8,304,596 B2
(45) Date of Patent: Nov. 6, 2012

(54) FECAL SAMPLING DEVICE AND METHOD

(75) Inventor: Vincent LaStella, Clark, NJ (US)

(73) Assignee: Immunostics, Inc., Ocean, NJ (US)

( * ) Notice: Subject to any disclaimer, the term of this patent is extended or adjusted under 35 U.S.C. 154(b) by 1128 days.

(21) Appl. No.: 12/101,813

(22) Filed: Apr. 11, 2008

(65) Prior Publication Data
US 2009/0259142 A1 Oct. 15, 2009

(51) Int. Cl.
A61F 13/15 (2006.01)
A61F 13/20 (2006.01)
A61B 10/00 (2006.01)
A61B 5/00 (2006.01)
B65D 81/00 (2006.01)
G01N 21/75 (2006.01)
G01N 31/22 (2006.01)
G01N 33/52 (2006.01)
B01L 3/00 (2006.01)

(52) U.S. Cl. ............ 604/358; 604/385.01; 604/385.05; 604/385.101; 604/385.11; 604/385.13; 604/385.201; 604/389; 604/390; 600/562; 600/573; 422/409; 422/430

(58) Field of Classification Search .................. 600/562, 600/573, 580; 604/358–361, 378, 381, 385.01, 604/385.05, 385.06, 385.08, 385.101, 385.11, 604/385.13, 385.14, 385.201, 389, 390; 436/66; 422/409
See application file for complete search history.

(56) References Cited

U.S. PATENT DOCUMENTS

| 2,291,173 | A | 7/1942 | Simpson | 40/702 |
| 3,996,006 | A | 12/1976 | Pagano | 23/253 |
| 4,092,120 | A | 5/1978 | Suovaniemi et al. | 422/56 |
| 4,112,165 | A | 9/1978 | Russell | 428/134 |
| 4,225,557 | A | 9/1980 | Hartl et al. | 422/56 |
| 4,259,964 | A | 4/1981 | Levine | 600/371 |
| 4,273,741 | A | 6/1981 | Levine | 422/56 |

(Continued)

FOREIGN PATENT DOCUMENTS

EP 0 269 362 A 6/1988

(Continued)

OTHER PUBLICATIONS

Extended European Search Report (Apr. 4, 2006).

(Continued)

Primary Examiner — Jeffrey G Hoekstra
Assistant Examiner — Devin Henson
(74) Attorney, Agent, or Firm — Stroock & Stroock & Lavan LLP

(57) ABSTRACT

A fecal sample collecting device and method. The device of an embodiment includes a removable first layer, having primary and secondary apertures and a second layer having a releaseable adhesive on an inner surface that secures the first and second layers, a flap aligned with the primary aperture, and an integrally formed removable tab. The device also includes a sheet between the two layers. In a first configuration, the sheet is aligned with the primary aperture such that a sample is deposited thereon when the device is used to wipe one's anus, and the removable tab is aligned with the secondary aperture such that a second sample is deposited thereon. Subsequently, the first layer is discarded, thereby exposing the adhesive on the inner surface of the second layer. The device is placed in a second configuration by folding the inner surface upon itself. Thus, primary and secondary samples are enclosed.

37 Claims, 4 Drawing Sheets

U.S. PATENT DOCUMENTS

| | | | |
|---|---|---|---|
| 4,333,734 A | 6/1982 | Fleisher | 436/66 |
| 4,365,970 A | 12/1982 | Lawrence et al. | 436/66 |
| 4,367,750 A | 1/1983 | Levine | 600/371 |
| 4,420,353 A | 12/1983 | Levine | 156/227 |
| 4,427,769 A | 1/1984 | Aldercreutz et al. | 435/7 |
| 4,486,536 A | 12/1984 | Baker et al. | 436/66 |
| D281,903 S | 12/1985 | Duffy | D24/225 |
| 4,559,949 A | 12/1985 | Levine | 600/371 |
| 4,615,982 A | 10/1986 | Lawrence | 436/66 |
| 4,645,743 A | 2/1987 | Baker et al. | 436/66 |
| 4,789,629 A * | 12/1988 | Baker et al. | 435/7.92 |
| 4,804,518 A | 2/1989 | Levine et al. | 422/56 |
| 4,808,379 A * | 2/1989 | Wardlaw et al. | 422/430 |
| 4,818,702 A | 4/1989 | Lawrence | 436/66 |
| 4,820,646 A | 4/1989 | Lawrence | 436/66 |
| 4,937,197 A | 6/1990 | Lawrence | 436/66 |
| 4,939,097 A | 7/1990 | Lawrence | 427/96.9 |
| 4,942,132 A | 7/1990 | Lawrence | 436/66 |
| 4,971,914 A | 11/1990 | Lawrence | 436/66 |
| 5,053,342 A | 10/1991 | Lawrence | 436/66 |
| 5,064,766 A | 11/1991 | Wardlaw et al. | 436/66 |
| 5,068,197 A | 11/1991 | Lawrence | 436/66 |
| 5,094,956 A | 3/1992 | Grow et al. | 436/66 |
| 5,100,619 A * | 3/1992 | Baker et al. | 422/408 |
| 5,106,582 A | 4/1992 | Baker | 422/58 |
| 5,150,971 A | 9/1992 | Strong et al. | 383/84 |
| 5,171,529 A | 12/1992 | Schreiber | 422/58 |
| 5,192,501 A | 3/1993 | Guadagno et al. | 422/56 |
| 5,196,167 A | 3/1993 | Guadagno et al. | 436/66 |
| 5,198,365 A | 3/1993 | Grow et al. | 436/66 |
| 5,215,713 A | 6/1993 | Steinbiss et al. | 422/61 |
| 5,217,874 A | 6/1993 | Guadagno et al. | 435/28 |
| 5,264,181 A | 11/1993 | Schreiber | 422/58 |
| 5,273,888 A | 12/1993 | Guadagno | 436/66 |
| 5,310,680 A | 5/1994 | Baker et al. | 436/66 |
| D351,475 S | 10/1994 | Gerber | D24/223 |
| 5,391,498 A | 2/1995 | Baker et al. | 436/66 |
| 5,411,893 A | 5/1995 | Eden et al. | 422/58 |
| 5,447,868 A | 9/1995 | Augurt | 436/66 |
| 5,563,071 A | 10/1996 | Augurt | 436/66 |
| D383,215 S | 9/1997 | Levy | D24/225 |
| 5,702,913 A | 12/1997 | Guadagno | 435/28 |
| 5,747,344 A | 5/1998 | Cleator | 436/66 |
| 5,747,351 A | 5/1998 | Hemmati | 436/514 |
| 5,948,687 A | 9/1999 | Cleator | 436/66 |
| 6,006,911 A | 12/1999 | Levy | 206/456 |
| D423,110 S | 4/2000 | Cipkowski | D24/225 |
| D430,303 S | 8/2000 | Cipkowski | D24/225 |
| 6,221,678 B1 | 4/2001 | Chandler | 436/530 |
| 6,271,046 B1 | 8/2001 | Chandler | 436/530 |
| 6,410,336 B1 | 6/2002 | Augurt | 436/66 |
| 6,436,714 B1 | 8/2002 | Clawson et al. | 436/66 |
| 7,189,356 B1 | 3/2007 | Clawson | 422/56 |
| 7,288,413 B2 | 10/2007 | Goulden | 436/66 |
| 7,427,505 B2 * | 9/2008 | LaStella | 436/66 |
| 2004/0053417 A1 | 3/2004 | Sinsky | 436/164 |

FOREIGN PATENT DOCUMENTS

| | | |
|---|---|---|
| EP | 1 618 957 A | 1/2006 |
| EP | 1619 502 A1 | 1/2006 |
| WO | WO 90/03927 | 4/1990 |
| WO | WO 90/13819 | 11/1990 |
| WO | WO 00/54029 | 9/2000 |
| WO | WO 02/080775 | 10/2002 |

OTHER PUBLICATIONS

M. Beg,, et al; Occult Gastro-Intestinal Bleeding Detection, Interpretation, and Evaluation; Department of Medicine JN Medical College—Aligarh & Dr. RML Hospital-New Delhi; web publication on www.indigene.com/gas/featArt/indGasFeat10.html; pp. 1-6.

Allison, J., et al., A Comparison of Fecal Occult-Blood Tests for Colorectal-Cancer Screening; New England Journal of Medicine. 334:155-9, Jan. 18, 1996; web publication on www.journalclub.org.

Website: www.insuretest.com, undated.

European Search Report, dated Jun. 9, 2009, for EP Application No. EP 09 15 7794.

* cited by examiner

FECAL SAMPLING DEVICE AND METHOD

FIELD OF THE INVENTION

The present invention relates, generally, to specimen collection and more particularly, a device for collecting and determining the presence of occult blood in fecal matter, a method of testing using such a device and a test kit containing such a device.

BACKGROUND OF THE INVENTION

Over 100,000 persons per year in the United States are afflicted with cancer of the colon and rectum. When the number of colon/rectal cancers occurring each year is combined with the number of cancers occurring in other digestive organs, including the esophagus and stomach, such cancers of the digestive system account for more occurrences of cancer than any other single form of the disease. Contrary to many other forms of cancer, early diagnosis and treatment of digestive tract cancer does result in a cure rate of 80% to 90%. If, however, the disease is not detected until the later stages, the cure rate drops significantly. Thus, early detection of the disease is important to successful treatment of digestive tract cancer.

Most, but not all, cancers of the digestive tract bleed to a certain extent. This blood is deposited on and in fecal matter excreted from the digestive system. The presence of blood in fecal matter is not normally detected, however, until gross bleeding, that is, blood visible to the naked eye, occurs. Gross bleeding, however, is symptomatic of advanced cancers.

Digestive tract cancers in the early stages, including precancerous polyps, also tend to bleed, giving rise to occult (hidden) blood in the fecal matter. Other pathological conditions, such as Crohn's disease and diverticulitis, can also give rise to the presence of occult blood in the fecal matter.

It is known that because of the relatively high fat content of fecal matter, blood, when present, is not distributed uniformly throughout it. For this reason, obtaining multiple samples from different areas of each bowel movement is desirable; but even a single positive test from any part of the feces should be considered a positive result.

Accordingly, test equipment and test procedures have been developed for use by physicians in testing for the presence of occult blood in fecal matter. Such tests frequently employ an absorbent paper impregnated with a guaiac reagent and encased in a special test slide having openable flaps. To use the test slide, a sample of fecal matter is smeared onto the guaiac-impregnated paper by opening a panel on one side of the test slide. Thereafter, the panel is closed. A panel on the opposite side of the test slide is then opened and a non-aqueous developing solution is applied to the guaiac-impregnated paper. If occult blood is present in the fecal matter smeared on the opposite side of the paper, the guaiac reaction will dye the paper blue, providing a positive indication of the presence of blood in the fecal matter.

Drawbacks of this type of test slide include risk of contamination from handling the test slides and a high percentage of false positives obtained from patients who in fact do not have a cancer or other condition for which occult blood is symptomatic. For example, certain foods, such as rare red meat and peroxidase enzymes as present in certain foods, such as horseradish, broccoli and cantaloupe, can cause a false positive result.

To cut down on false positives, physicians place patients on specific diets designed to restrict the intake of animal proteins and other sources of false positives. Despite these efforts, large numbers of false positives still occur, as compliance with the restricted diet is unreliable. A false positive result in the test often results in expensive follow-up testing of patients who in fact have simply consumed a lot of meat or other undesirable foods just prior to the test.

A specific test for human hemoglobin has been devised. This test, offered by SmithKline Diagnostics under the tradename HEMESELECT, theoretically registers only human hemoglobin and not animal blood from meat or other agents, and therefore, theoretically does not require the patient to be on a special diet. While the hemoglobin test has the advantage over guaiac tests of registering only human hemoglobin, the hemoglobin test is expensive for a screening test and requires specially trained individuals to perform and read the test. Furthermore, hemoglobin tests are typically very sensitive, capable of detecting as little as 0.3 micrograms of blood, which is in excess of what a healthy normal person loses in fecal matter daily. Thus, because even healthy individuals lose a small amount of blood, which can be detected, a positive result may itself be a false positive leading to further costly, unnecessary tests and procedures.

Another drawback of this type of test is that follow-up tests commonly result in reduced patient compliance. Having already completed one test, a patient may be unwilling or unable to return in a timely fashion for follow-up tests. Consequently, the physician may be deprived of data necessary to accurately diagnose the patient.

A need therefore exists for a relatively inexpensive test that has a minimal incidence of false positives and minimal manipulation of the sample. A further need exists for a test that improves patient compliance should follow-up testing be required.

SUMMARY OF THE INVENTION

Embodiments of the present invention satisfy the foregoing and other needs. For example, a fecal sampling device according to one embodiment may be a sheet of paper with an adhesive, where one half of the sheet includes a flap and a removable tab. On top of the adhesive sheet of paper, there should be disposed at least two non-adhesive pieces of paper, one on each half. On the half of the adhesive sheet of paper that contains the flap and the tab portions, the non-adhesive piece of paper should cover the tab portion, and include a portion that may move with the tab portion. The non-adhesive piece of paper should also have a section that covers the tab portion and is configured to receive a fecal sample. Additionally, the non-adhesive sheet of paper preferably covers one of the borders of the first half.

The non-adhesive piece of paper on the second half of the adhesive sheet preferably matches the first sheet such that when the device is folded along the boundary between the first and the second half of the adhesive sheet, the non-adhesive papers on the second half overlay the non-adhesive paper on the first half. Both pieces of non-adhesive paper should be configured so as not to cover the entire adhesive layer on the adhesive paper.

Further, on top of the first half of the adhesive paper, above the non-adhesive piece of paper, there should be located, an absorbent piece of paper that is configured to receive a fecal sample and is sized to overlay the first piece of paper, and adhere to the adhesive on the first piece of paper.

Additionally, overlaying all of the elements above, there is preferably a tissue paper that is the same size as the adhesive paper. The tissue paper should be placed so as to overlay the adhesive paper and adhere to the adhesive. The tissue paper should have separate apertures above the absorbent sheet and above the removable tab.

In use, the patient should be able to take the device and wipe, after defecation, such that fecal matter gets deposited on the tissue paper, and through the tissue paper onto the removable tab and the absorbent sheet. Afterwards the patient should peel off the tissue paper, discard it, and fold the device along the border between the two halves. This should cause the enclosing of the fecal matter, deposited on the removable tab and the absorbent sheet, by the piece of paper located on the second half, and the sealing of the two halves of the device together, by the adhesive on the adhesive sheet.

Subsequently the patient should deliver the device to a doctor who may in turn peel the tab portion to reveal the absorbent sheet underneath. The doctor may deposit a developing solution onto the absorbent sheet in order to determine presence of occult blood in the fecal sample. Additionally, the doctor may remove the tab that contains another fecal sample, and perform a different test on that sample.

In an alternate embodiment, the fecal sampling device may be a sheet of paper with an adhesive, where one half of the sheet includes a removable tab section. On top of the adhesive sheet of paper, overlaying the removable tab section, there should be disposed a sheet of plain filter paper. The sheet of plain filter paper preferably adheres to the removable tab section and the half of the adhesive sheet of paper that contains the removable tab section. Both the removable tab section and the filter paper may contain complementary perforations such that removal of the removable tab section results in the removal of a section of the filter paper that overlies the removable tab section. It will be apparent to those skilled in the art that instead of filter paper any other material capable of receiving a fecal sample may be used.

Additionally, overlaying all of the elements above, there is preferably a tissue paper that is the same size as the adhesive paper. The tissue paper should be placed so as to overlay the adhesive paper and adhere to the adhesive. The tissue paper should have an aperture over the removable tab section.

In use, the patient should be able to take the device and wipe, after defecation, such that fecal matter gets deposited on the tissue paper, and through the aperture of the tissue paper onto the filter paper overlaying the removable tab. Afterwards the patient should peel off the tissue paper, discard it, and fold the device along the border between the two halves. This should cause the sealing of the fecal matter inside the fecal sampling device, by the adherence of the two halves of the device together, by the adhesive on the adhesive sheet of the device. Finally, the patient should deliver the sealed device to a doctor.

The doctor may remove the tab section, along with the filter paper attached to that tab section, and the fecal sample disposed on the filter paper. Thereafter, the doctor may perform various test upon the fecal sample. After removing the tab, the doctor should dispose of the device.

BRIEF DESCRIPTION OF THE DRAWINGS

The devices and methods according to various embodiments are explained in greater detail using the following exemplary drawings. The drawings are merely illustrative of the structure of devices and certain features that may be used singularly or in combination with other features. Thus, the invention is not limited to the embodiments shown or described.

DETAILED DESCRIPTION OF EMBODIMENTS

Certain embodiments of the invention will now be described with reference to the drawings. In general, such embodiments relate to a fecal sampling device, including by way of non-limiting example, a device for collecting and determining the presence of occult blood in both a primary and secondary sample of fecal matter. The invention may have other applications and uses and should not be limited to the structure or use described and illustrated.

Figure 1:
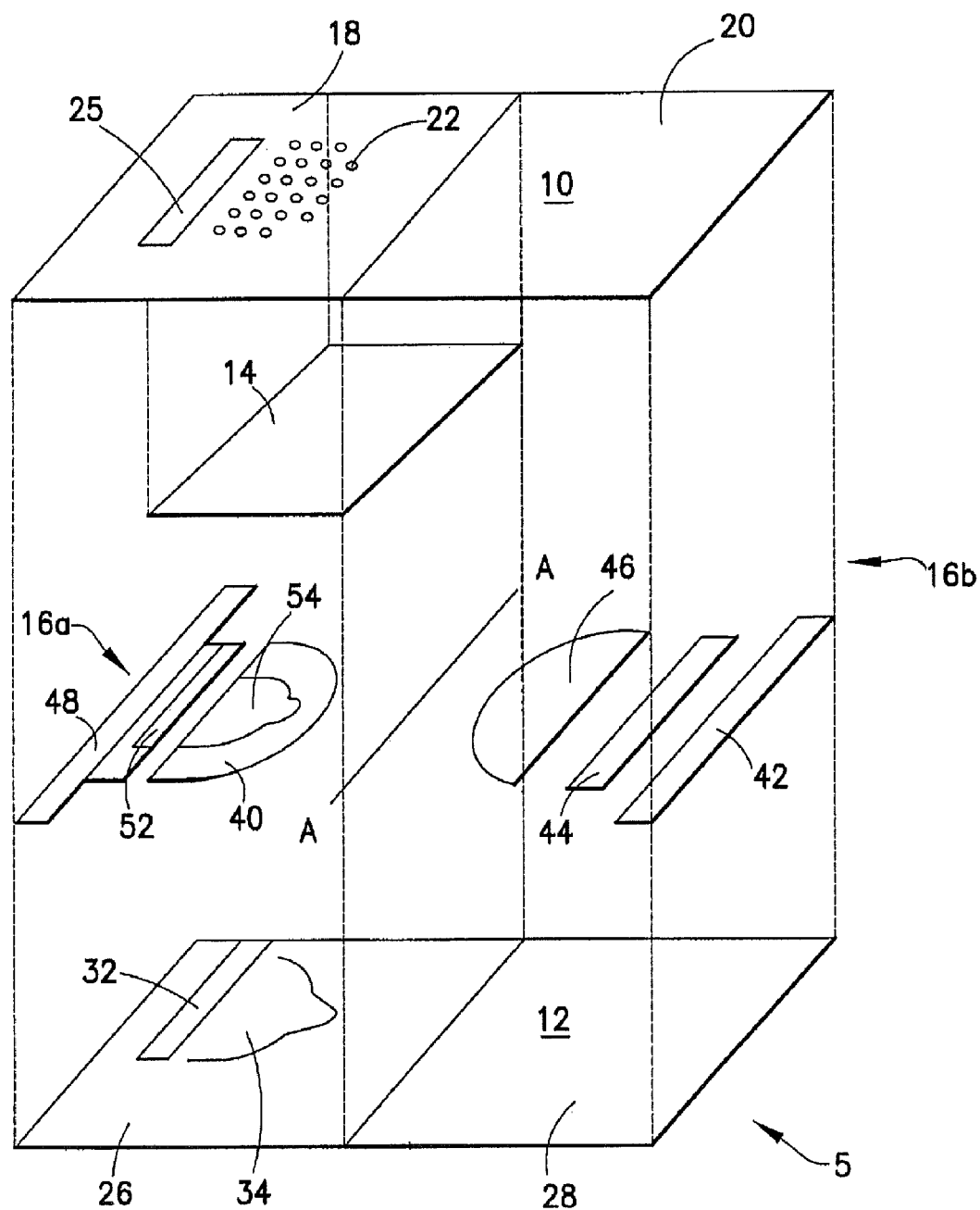
FIG. 1 is an exploded perspective view of one embodiment of a fecal sampling device according to the present invention.

As shown in FIG. 1, the fecal sampling device 5 according to one embodiment of the invention may include a tissue layer 10 and an outer layer 12, with an absorbent sheet 14 and a plurality of barrier pieces 16a, 16b disposed between the outer layer 12 and tissue layer 10. When device 5 is assembled for use, tissue layer 10 and outer layer 12 essentially overlay each other, with sheet 14 interposed therebetween.

The tissue layer 10 generally includes a first portion 18 and a second portion 20. In addition, the tissue layer 10 may include a plurality of metering holes 22 and an aperture 25 on one of the portions 18, 20 thereof (shown as the first portion 18), through which primary and secondary samples of a specimen may be received, respectively. The tissue layer 10 is preferably a moisture or liquid barrier, thus limiting the sample passing through to only the areas corresponding to the aperture 25 and holes 22. As such, tissue 10 may be any suitable material, such as wax paper, polypropylene, biaxially oriented polypropylene (BOPP), and biaxially oriented polypropylene terephtalate polyester sold under the trademark MYLAR®.

Figure 2:
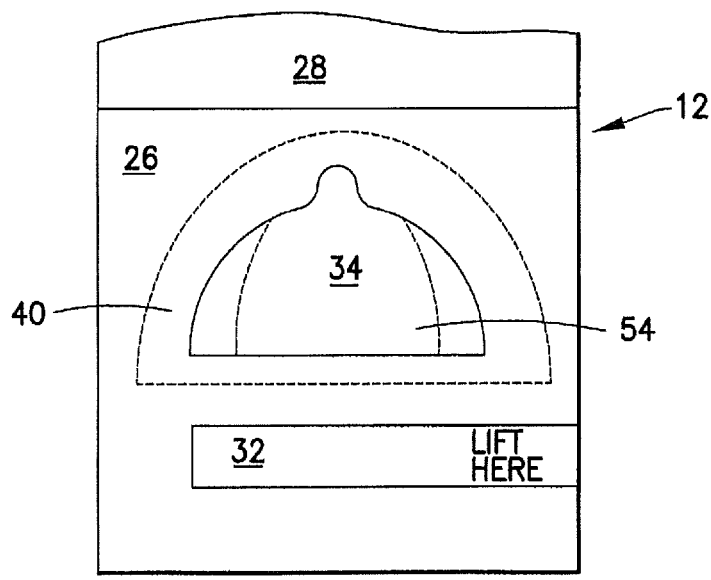
FIG. 2 is a top plan view of a portion of the fecal sampling device of FIG. 1.
Figure 3:
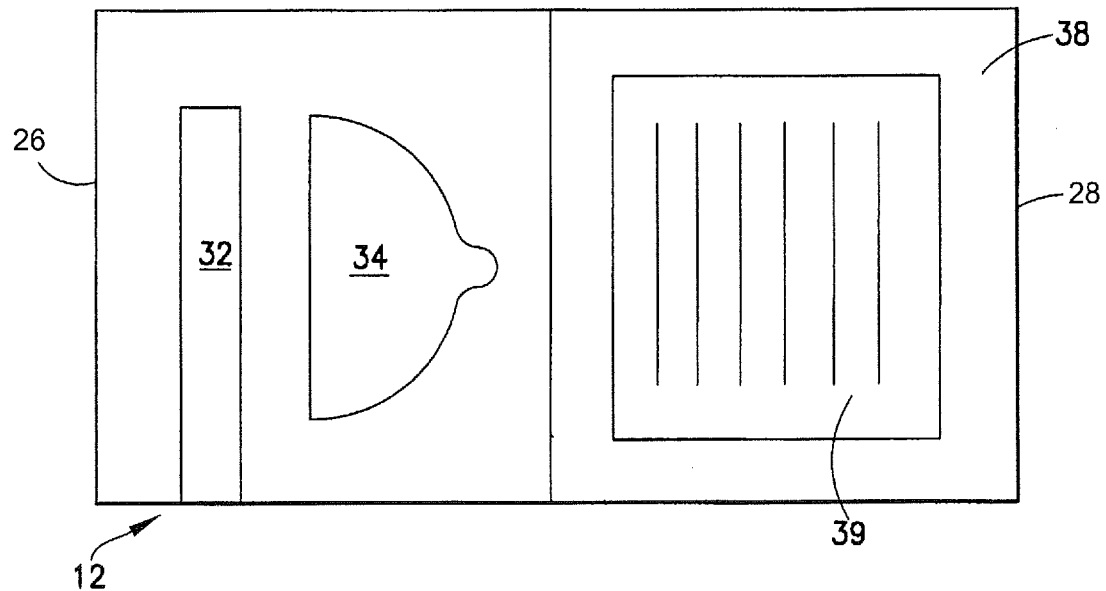
FIG. 3 is a top plan view of the fecal sampling device of FIG. 1.
Figure 6:
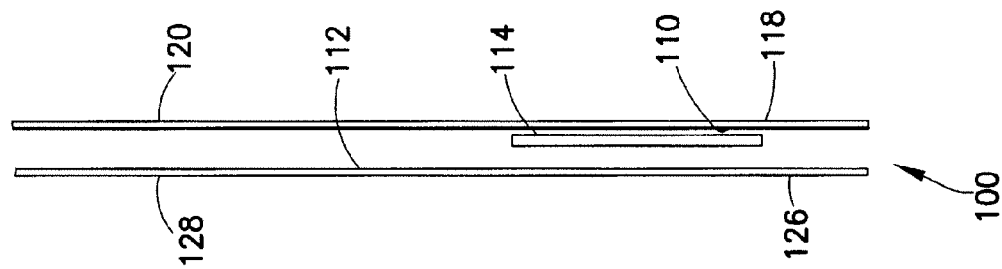
FIG. 6 is an exploded side view of the embodiment of FIG. 4.
Figure 5:
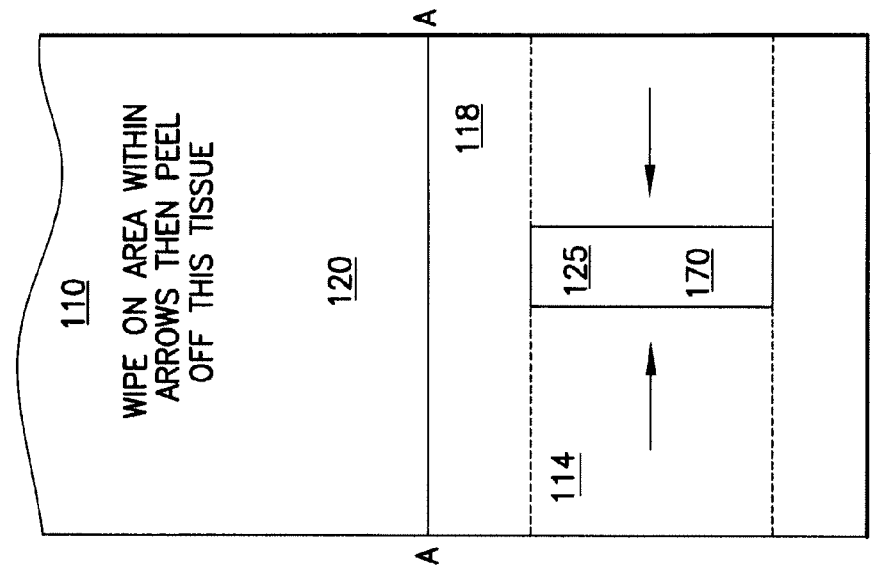
FIG. 5 is a back plan view of the embodiment of FIG. 4.
Figure 4:
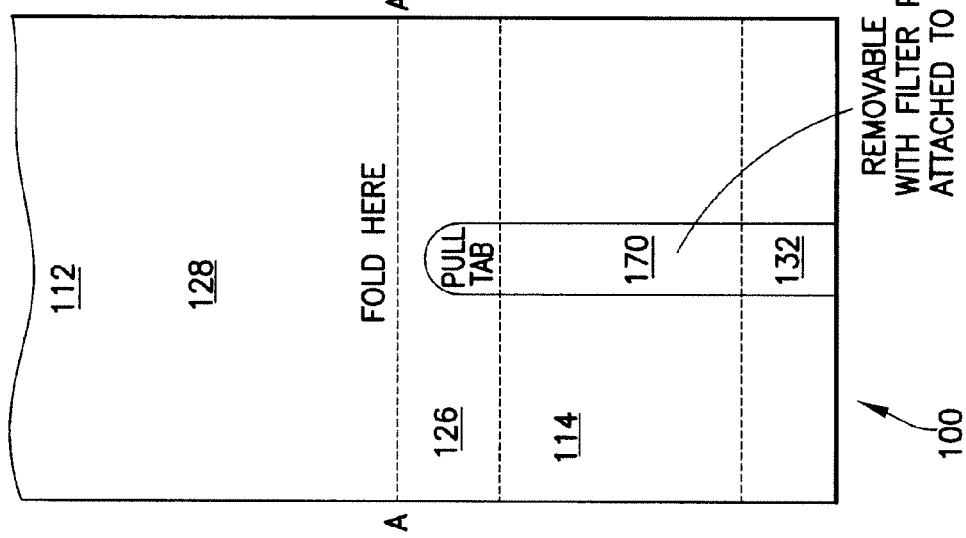
FIG. 4 is a front plan view another embodiment of a fecal collection device according to the present invention.
Figure 7:
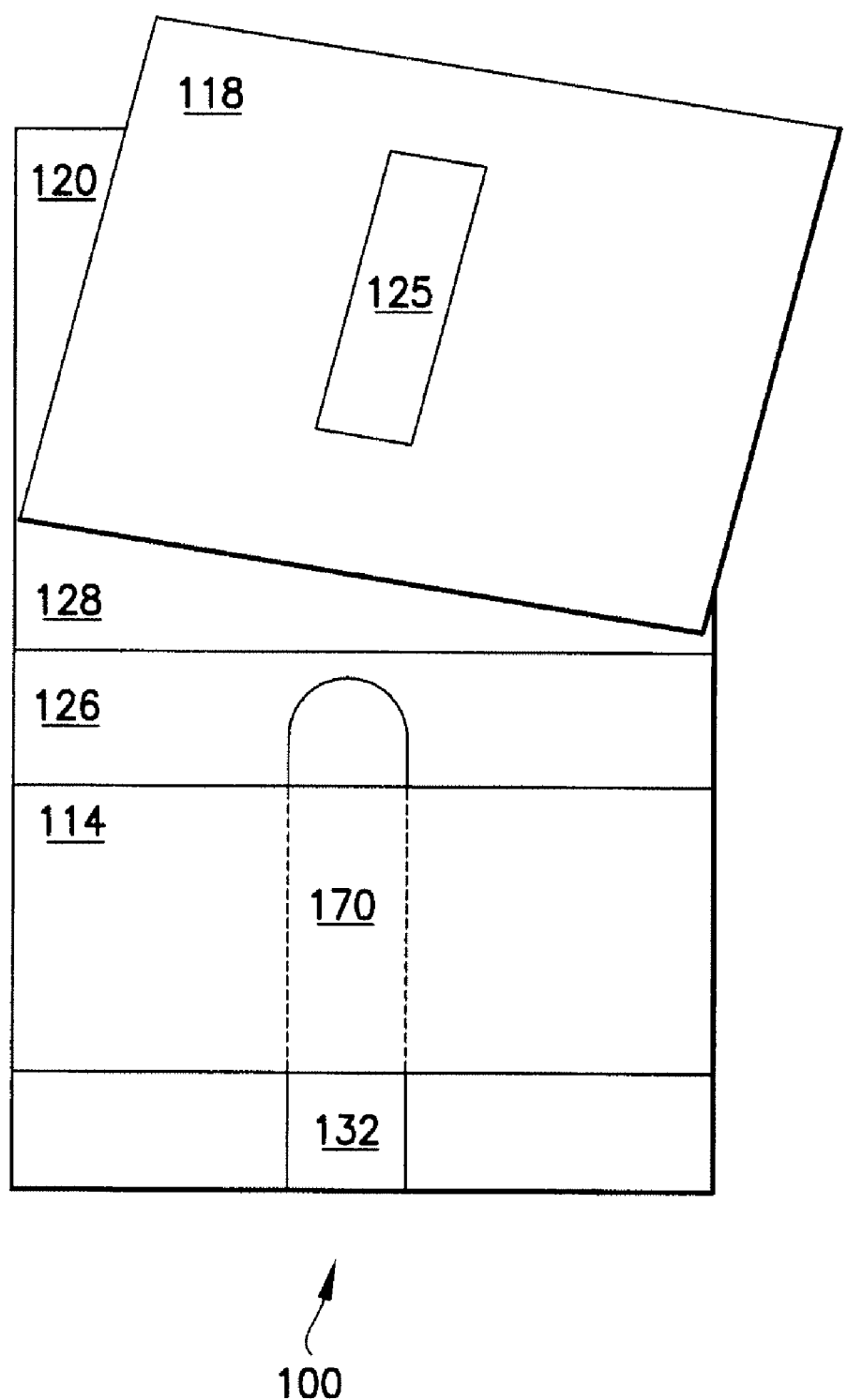
FIG. 7 is a front plan view of the embodiment of FIG. 4, with the removable layer partially removed.

The outer layer 12 also generally includes a first portion 26 and a second portion 28. When device 5 is assembled, the first portion 26 of the outer layer 12 overlays the first portion 18 of the tissue layer 10, and the second portion 28 of the outer layer 12 overlays the second portion 20 of the tissue layer 10. One of the portions 26, 28 (shown as the first portion 26) may include a first flap 34 dimensioned to align with the plurality of holes 22 in the tissue layer 10, and a removable tab 32 dimensioned to align with the aperture 25 in the tissue layer 10. Thus, the removable tab 32 forms a part of a well for receiving a sample through aperture 25. The removable tab 32 is preferably formed from, and as a part of, the outer layer 12. Tab 32 is integrally formed as part of the outer layer 12 by die cutting or other method and can be formed either entirely or partially by perforations in outer layer 12. It should be understood that in certain embodiments the removable tab 32 may have a sheet overlaying and attached (e.g., adhered) to it, such that the sheet in fact receives the sample through aperture 25, and the sheet is removable along with the removable tab 32 (in certain embodiments this sheet may be a separate sheet or a section of sheet 14). In the present embodiment, the outer layer 12 may be coated with adhesive on its inner surface (i.e., the surface facing tissue layer 10). As discussed in greater detail below, the adhesive may permit the outer layer 12 to bond to the plurality of pieces 16a, 16b, the absorbent sheet 14, and the tissue layer 10. As shown in FIG. 2, the outer surface of outer layer 12 may preferably include a label 39 for patient information and/or instructions to the user.

In the present embodiment, as illustrated in FIG. 1, the absorbent sheet 14 may be a single piece of filter paper generally dimensioned to align with or overlay, the plurality of holes 22 of the tissue layer 10 when device 5 is assembled. The sheet 14 may be impregnated with guaiac reagent or another indicator selected based on the particular application of the devices. The device 5 may further include a wax, glue or other moisture barrier, for example, disposed on the absorbent sheet 14 itself or around the perimeter of the absorbent sheet 14 on the first portion 26 of the outer layer 12. This barrier separates the primary sample and sheet 14 from the secondary sample and the removable tab 32, thereby reducing the risk of contamination of the secondary sample on removable tab 32 by the elements of the primary sample and the primary test, such as guaiac and developer solution.

The plurality of pieces 16a, 16b are generally made of non-porous paper, such as, for example, wax paper, and function to define areas and prevent the adhesive disposed on the outer layer 12 from adhering to certain portions of the device 5. The first set of pieces 16a may include first 40, second 48 and third 52 pieces. As shown in FIGS. 1 and 2, the first piece 40 may be sized and configured to cover the flap 34 plus an additional area surrounding flap 34 of the outer layer 12, such that the first piece 40 adheres to the other layer 12 (including when flap 34 is opened). First piece 40 includes a flap section 54 partially defined by a die cut, which generally corresponds to and adheres to the flap 34. The adhesive on the inner surface of flap 34 allows it to removably adhere to a portion of the first piece 40, thereby assisting flap 34 to stay shut until purposefully opened.

The second piece 48 is generally dimensioned such that, when the device 5 is assembled, it aligns with and overlays the edge of the first portion 26 of the outer layer 12.

The device 5 may optionally include a third piece 52 generally positioned and dimensioned such that, when the device 5 is assembled, the third piece 52 adheres the removable tab 32 of the outer layer 12. Removal of the removable tab 32 also removes the third piece 52 which would carry the secondary sample.

The second set of pieces 16b generally includes three pieces 42, 44 and 46 that adhere to the second portion 28 of the outer layer 12 when the device is assembled and, when the device is folded along median axis A-A, correspond to and align with the pieces 48, 52, and 40 of the first set 16a. More specifically, and as described below, when the device 5 is used, it is folded along axis A-A, which causes pieces 40 and 46 to generally align, pieces 44 and 42 to generally align and piece 44 and removable tab 32 to generally align. As such, when the device 5 is used and folded along axis A-A, the primary sample deposited through holes 22 onto sheet 14 are preserved and prevented from adhering to the inner surface of outer layer 12 by piece 46. Similarly, the secondary sample is preserved and protected from adhering to outer layer 12 by piece 44. Pieces 42 and 48 provide non-adhesive grasping areas.

In alternate embodiments the device may not be symmetrical along the median axis A-A, and the device may be any size or shape. For example, the first portion 18 may be smaller than the second portion 20, and the second portion 20, may fold over portion 18, and around portion 18, such that the perimeter of section 20, adheres to the back of the first portion 26 to more securely seal the device.

When the device 5 is assembled, the pieces 16a, 16b adhere to the adhesive on the inner surface of the outer layer 12. Similarly, the sheet 14 adheres to the adhesive on the inner surface of the outer layer 12 along the edges of the sheet 14 that extend beyond the first set of pieces 16a. The holes 22 in the tissue layer 10 in conjunction with the sheet 14 define wells for receiving the primary sample, the holes 22 providing a metering of the amount and configuration of sample deposited on the sheet 14, and the aperture 25 in the tissue layer 10 in conjunction with the removable tab 32 (or any piece adhered thereto, if used) define a well for the secondary sample. In certain embodiments, the aperture 25 aligns with only a first portion of removable tab 32, leaving a second portion of removable tab 32 specimen-free, which serves as a grasping area. Such specimen-free grasping area helps prevent contamination and cross-contamination when being handled.

In use, a user, such as a patient, wipes after a bowel movement, grasping the second portions 20, 28 of the tissue and outer layers 10, 12 thereby depositing fecal samples on the first portion 18 of the tissue layer 10 and through the holes 22 and aperture 25. The fecal sample that passes through the holes 22—the primary sample—is deposited on the absorbent sheet 14. The fecal sample that passes through the aperture 25—the secondary sample—is deposited on the removable tab 32 of the outer layer 12. It should be understood that reference to a sample being deposited on the removable tab, or other portion, includes the sample being deposited directly on the removable tab or on a dry sheet of paper adhered to it and forming a part of it. Pieces 48, 42 which align with and adhere to the distal edges of the first and second portions 26, 28 prevent the edges of the tissue layer 10 from adhering to the outer layer 12, and hence permit the user to easily grasp and peel away the tissue layer 10 from the outer layer 12 after wiping. Removing the tissue layer 10 exposes the adhesive on the surface of outer layer 12. The user may then dispose of the tissue layer 10 and fold the outer layer 12 along its medial axis A-A. This results in piece 46 overlapping the primary fecal sample that has been deposited on the absorbent sheet 14, and piece 44 overlapping the secondary fecal sample that has been deposited on the removable tab 32. Sections of the inner portion of the outer layer 12 which are not overlapped by one of the non-adhesive pieces 40, 52, 48, 46, 44, 42, 54 will subsequently adhere to either the absorbent sheet 14 or other sections of the outer layer 12, thereby sealing the sampling device 5. Because the outer layer 12 includes an adhesive folding device 5 along axis A-A creates sealed pockets containing fecal samples, which may be preserved until testing by a doctor.

A physician receiving the device 5 may then peel back the flap 34 to perform a primary test to check for blood in the primary sample. For example, if the absorbent sheet is permeated with guaiac solution, the physician may drop hydrogen peroxide or other developing solution on the absorbent sheet. The presence of occult blood will be determined by a change in color of the absorbent sheet. The device may also include a control area on the sheet 14 to provide an indication of proper positive and/or negative results (e.g., confirming the effectiveness of the guaiac and/or developing solution).

If the primary test is "positive," a confirmatory, secondary test may be performed. If a secondary analysis is desired, the physician may subsequently remove the removable tab 32, and conduct further analysis on the fecal sample deposited on the tab 32 using, for example a more specific immunological test. Such a test may involve removing the tab 32 and depositing it into a test tube or other container. Thus, the secondary test is performed off-device, whereas the primary test is performed on-device.

It should be appreciated that the device provides several advantages over the prior art. For example, the removable tab is capable of being removed from the device (and particularly the exterior of the device) and used in its entirety in a subsequent, secondary analysis. Thus, there is no further manipulation of the removable tab once it has been pulled away from the device, thereby reducing the likelihood of sample cross-contamination and end-user (both patient and physician/laboratory technician) contamination. Furthermore, because the device obtains both a primary sample and a secondary sample at the same time and with a single act of the patient, there is no need to go back to a patient with a positive primary test for an additional sample, and patient non-compliance is avoided.

In alternate embodiments the aperture 25 may include a plurality of holes, similar to holes 22. In alternate embodiments of the invention, it is possible for all the non-adhesive pieces 16a to be integral as one sheet, in which case the tab 52, will need to be cut out by a physician, alternatively, perforation may be provided in order to facilitate removal of tab 52.

It will be clear to one skilled in the art that different sizes, different types, and different numbers (including none) of pieces 16a, 16b may be used. Additionally, multiple removable tabs may be incorporated into the fecal sampling device in case more than two tests are expected to be performed.

Turning now to FIGS. 4-7, an alternate embodiment for collecting fecal samples by wiping the device across a user's anus will now be discussed. As shown in FIG. 4-7, the fecal sampling device 100, like the prior embodiments, may include a tissue layer 110 and an outer layer 112, with a sheet of plain filter paper 114, which is not impregnated with guaiac or other reagent for performing a test for the presence of blood, disposed between the outer layer 112 and tissue layer 110. When device 100 is assembled for use, tissue layer 110 and outer layer 112 substantially overlay each other, with the filter paper sheet 114 interposed therebetween.

The tissue layer 110 generally includes a first portion 118 and a second portion 120. In addition, the tissue layer 110 includes an aperture 125 on one of the portions 118, 120 thereof (shown as the first portion 118), through which a sample may be received. The tissue layer 110 is preferably a moisture or liquid barrier, thus limiting the sample passing through to only the area corresponding to the aperture 125. As such, tissue 110 may be any suitable material, such as wax paper, polypropylene, biaxially oriented polypropylene (BOPP), and biaxially oriented polypropylene terephtalate polyester sold under the trademark MYLAR®. In alternate embodiments, aperture 125 (like aperture 25 in the aforementioned embodiments) is replaced with a plurality of apertures for metering the amount of the sample received.

The outer layer 112 also generally includes a first portion 126 and a second portion 128. When device 100 is assembled, the first portion 126 of the outer layer 112 overlays the first portion 118 of the tissue layer 110, and the second portion 128 of the outer layer 112 overlays the second portion 120 of the tissue layer 110. One of the portions 126, 128 (shown as the first portion 126) may include a removable tab 132 that is dimensioned to align with the aperture 125 in the tissue layer 110. As with the aforementioned embodiments, the aperture 125 may align with only a portion of removable tab 132, thereby leaving a specimen-free grasping area to help prevent contamination. The removable tab 132 is preferably formed from, and as a part of, the outer layer 112. Thus, tab 132 is integrally formed as part of the outer layer 112 for example, by die cutting or other method and can be formed either entirely or partially by perforations in outer layer 112. It should be understood that in certain embodiments the removable tab 132 may have a sheet overlaying and attached to it, such that the sheet in fact receives the sample through aperture 125, and the sheet is removable along with the removable tab 132. The outer layer 112 may be coated with a releasable adhesive on all or a portion of its inner surface (i.e., the surface facing tissue layer 110). As discussed in greater detail below, the adhesive may permit the outer layer 112 to bond to the sheet of filter paper 114, and the tissue layer 110.

In the present embodiment, as partially illustrated in FIGS. 4-7, the filter paper sheet 114 may be a single sheet of plain filter paper generally dimensioned to align with or overlay a portion of the removable tab section 132 that aligns with the aperture 125 when device 165 is assembled. The filter paper sheet 114 may further include a removable section 170, that is sized and configured to overlay the removable tab section 132 and the aperture 125. The removable section 170 of filter paper sheet 114, may be integrally formed as part of the filter paper sheet 114, for example, by die cutting or other method and can be formed either entirely or partially by perforations in the filter paper sheet 114. Alternatively, the entire filter paper sheet 114 may be sized and configured to overlay the removable tab 132 (or a portion thereof) and the aperture 125 without substantially encroaching on the rest of the area of outer layer 112, thus the entire filter paper sheet 114 may become removable with the removable tab 132.

In use, a user, such as a patient, wipes with device 100, after a bowel movement, thereby depositing a fecal sample on the first portion 118 of the tissue layer 110 and through the aperture 125. The fecal sample that passes through the aperture 125 is deposited on the removable section 170 of the filter paper 114, which is attached to the removable tab 132. The user may, after wiping, peel away the tissue layer 110 from the outer layer 112 and discard it. Removing the tissue layer 110 exposes the adhesive on the surface of outer layer 112. The user may then fold the outer layer 112 along its medial axis A-A. This results in the adherence of section 126 of the outer layer 112 to section 128 of the outer layer 112, thereby sealing the sampling device 100 with the sample being sealed and retained therein. In one embodiment section 128 of layer 112 includes an additional, non-adhesive piece adhered to layer 112 that, when the device 100 is folded, aligns with the removable tab 32 so that the deposited sample does not adhere to the adhesive. Such piece may be filter paper, tissue paper or any other specimen absorbing and/or capturing material. Alternatively, the area of layer 112 that aligns with the removable tab 132 when the device 100 is folded has no adhesive.

A physician receiving the sealed device 100 may subsequently remove the removable tab 132, thereby also removing the removable section 170 of the filter paper sheet 114 that is adhered to the removable tab 132. The physician may then conduct analysis on the fecal sample deposited on the removable section 170 using any test such as H-Pylori, blood, etc. Such a test may involve depositing the removable tab 132, along with the removable section 170 of the filter paper sheet 114 (in embodiments where it is used) and sample, into a test tube or other container. Thus, device 100 serves the function of collecting a sample for off-device testing (i.e., once the sample is removed from the device).

In alternate embodiments, device 100 may include a plurality of non-adhesive pieces of material (not shown), similar to pieces 16a and 16b of FIG. 1, disposed between the tissue layer 110 and the outside layer 112. These pieces may be used as barrier pieces around or on top of the filter paper sheet 114 in order to, for example, prevent sample loss or contamination. These non-adhesive pieces may also be used to provide gripping areas for the user of the device 100. The non-adhesive pieces may further be positioned, as described above with reference to FIG. 1, such that folding of the device 100, after the removal of the tissue layer 110, creates a sealed pocket around a sample deposited on the removable portion 170 of filter paper sheet 114. Those skilled in the art will appreciate that various configurations of non-adhesive pieces may be used to accomplish various goals of promoting sanitary use of the device 100 and preservation of samples collected by device 100.

To ease the removability of the removable tab 32 or 132, second portions 28, 128 may be perforated or scored along its edge, where the second portion 28, 128 adheres to the removable tab 32, 132. As such, removal if the removable tab 32, 132 takes with it the section of the second portion 28, 128 that adheres to the removable tab 32, 132.

It will be clear to one skilled in the art that different sizes, different types, and multiple numbers of removable tabs may be incorporated into the fecal sampling device in the even that more than one test is to be performed.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. A wipe-type fecal sampling device for collecting primary and secondary fecal samples of a user during a wipe of the user's anus when the fecal sampling device is in a first configuration and sealing the collected samples when the fecal sampling device is in a second configuration, the fecal sampling device comprising:
   a removable first layer forming a first exterior surface of the fecal sampling device in the first configuration, the first layer including at least one primary aperture and at least one secondary aperture;
   a second layer forming a second exterior surface of the fecal sampling device when in the first configuration, the second layer including:
      an inner surface and a releasable adhesive on at least a portion of the inner surface at least partially securing the first layer to the second layer;
      a flap in the second layer aligned with the at least one primary aperture; and
      a removable tab integrally formed as part of the second layer on the second exterior surface of the device;
   at least one sheet between the first layer and the second layer when in the first configuration; and
   a first barrier piece;
   wherein in the first configuration:
      the at least one sheet is aligned with the at least one primary aperture, the at least one sheet configured and arranged such that the primary sample is deposited on the at least one sheet during the wipe;
      the removable tab is aligned with the at least one secondary aperture, the removable tab configured and arranged such that the secondary sample is deposited on the removable tab during the wipe; and
      the first barrier piece is between the first layer and the second layer; and
   wherein in the second configuration, subsequent to collection of the primary and secondary samples:
      the first layer is removed and discarded, thereby exposing the adhesive on the inner surface of the second layer;
      the inner surface of the second layer is folded upon itself such that the primary and secondary samples are enclosed in the fecal sampling device; and
      the removable tab and flap are on the second exterior surface of the fecal sampling device, the removable tab and flap both being accessible from the second exterior surface of the device; and
      the first barrier piece is aligned with the removable tab to prevent the secondary sample from adhering to the releasable adhesive.

2. The fecal sampling device of claim 1, wherein the primary aperture is a plurality of metering apertures.

3. The fecal sampling device of claim 1, wherein the removable tab further comprises a deposit area aligned with the at least one secondary aperture where the secondary sample is deposited, and a grasping area not aligned with the at least one secondary aperture and outside of the deposit area.

4. The fecal sampling device of claim 1, wherein the removable tab is demarcated at least in part by perforations.

5. The fecal sampling device of claim 4, wherein the removable tab is formed on a portion of the second layer that does not include the releasable adhesive.

6. The fecal sampling device of claim 1, wherein the removable tab is sized and configured to fit into a testing container.

7. The fecal sampling device of claim 6, wherein the testing container is a test tube.

8. The fecal sampling device of claim 1, wherein the at least one sheet is impregnated with guaiac.

9. The fecal sampling device of claim 1, wherein the fecal sampling device further includes:
   a second barrier piece disposed over the flap between the flap and the at least one sheet; and
   a third barrier piece disposed between the first and second layers;
   wherein when the fecal sampling device is placed in the second configuration the primary sample is disposed between the second and third barrier pieces.

10. The fecal sampling device of claim 9, wherein the at least one sheet includes a removable section adhered to the removable tab such that the secondary sample is deposited on the removable section.

11. The fecal sampling device of claim 10, wherein the removable section is demarcated at least in part by perforations.

12. The fecal sampling device of claim 9, wherein the at least one sheet comprises a first sheet and a second sheet, and wherein:
   the first sheet is configured and arranged such that the primary sample is deposited on the first sheet during the wipe, and the second sheet is disposed over and adhered to the removable tab such that the secondary sample is deposited on the second sheet during the wipe.

13. The fecal sampling device of claim 9, wherein the at least one sheet comprises one or more sheets for receiving a secondary sample disposed over and adhered to the removable tab, the one or more sheets for receiving a secondary sample configured and arranged such that the secondary sample is deposited thereon during the wipe.

14. The fecal sampling device of claim 1, wherein a portion of the flap section is demarcated by perforations.

15. A method of a user collecting primary and secondary fecal samples using the fecal sampling device of claim 1, the method comprising:
applying the fecal sampling device in the first configuration to the anus;
depositing a primary sample through the at least one primary aperture onto the at least one sheet;
depositing a secondary sample through the secondary aperture onto the removable tab;
placing the fecal sampling device in the second configuration by:
removing and discarding the first layer;
folding the second layer on itself such that the primary and secondary fecal samples are enclosed within the fecal sampling device.

16. The method of claim 15, the method further comprising:
writing patient information on the exterior of the fecal sampling device;
delivering the fecal sampling device to a doctor.

17. The method of claim 15, wherein the primary aperture is a plurality of metering apertures.

18. The method of claim 15, wherein the fecal sampling device further comprises a deposit area aligned with the at least one secondary aperture where the secondary sample is deposited, and a grasping area not aligned with the at least one secondary aperture and outside of the deposit area.

19. The method of claim 15, wherein the removable tab of the fecal sampling device is demarcated at least in part by perforations.

20. The method of claim 19, wherein the removable tab is formed on a portion of the second layer that does not include the releasable adhesive.

21. The method of claim 15, wherein the fecal sampling device further includes:
a second barrier piece disposed over the flap between the flap and the at least one sheet; and
a third barrier piece disposed between the first and second layers;
wherein when the fecal sampling device is placed in the second configuration the primary sample is disposed between the second and third barrier pieces.

22. The method of claim 21, wherein the at least one sheet includes a removable section adhered to the removable tab such that the secondary sample is deposited on the removable section.

23. The method of claim 22, wherein the removable section is demarcated at least in part by perforations.

24. The method of claim 21, wherein the at least one sheet comprises a first sheet and a second sheet, and wherein:
the first sheet is configured and arranged such that the primary sample is deposited on the first sheet during the wipe, and
the second sheet is disposed over and adhered to the removable tab such that the secondary sample is deposited on the second sheet during the wipe.

25. The method of claim 21, wherein the at least one sheet comprises one or more sheets for receiving a secondary sample disposed over and adhered to the removable tab, the one or more sheets for receiving a secondary sample configured and arranged such that the secondary sample is deposited thereon during the wipe.

26. A method of testing a fecal specimen using the fecal sampling device of claim 1, the method comprising:
receiving the device in the second configuration following collection of the primary sample and the secondary sample;
opening the flap to expose the at least one sheet containing the primary sample;
performing a primary test on the primary sample, the primary test being performed on the device; and
confirming results of the primary test by performing a secondary test, the secondary test being performed off of the device and including:
removing the removable tab containing the secondary sample from the second exterior of the fecal sampling device; and
performing a secondary test on the secondary sample contained on the removable tab after the removable tab has been removed from the device.

27. The method of claim 26, wherein the primary aperture is a plurality of metering apertures.

28. The method of claim 27, wherein the removable tab is integrally formed from a portion of the second layer that does not include the releasable adhesive.

29. The method of claim 26, wherein the removable tab further comprises a deposit area aligned with the at least one secondary aperture where the secondary sample is deposited, and a grasping area not aligned with the at least one secondary aperture and outside of the deposit area, the removable tab of the fecal sampling device is demarcated by perforations, and wherein removing the removable tab comprises:
holding the removable tab by the grasping area; and
manually tearing the removable tab via the perforations from the second exterior of the fecal sampling device.

30. The method of claim 26, wherein the removable tab is sized and configured to fit into a testing container.

31. The method of claim 26, wherein the at least one sheet includes a removable section adhered to the removable tab such that the secondary sample is deposited on the removable section.

32. The method of claim 31, wherein the removable section is demarcated at least in part by perforations.

33. The method of claim 26, wherein the at least one sheet comprises a first sheet and a second sheet, and wherein:
the first sheet is configured and arranged such that the primary sample is deposited on the first sheet during the wipe, and
the second sheet is disposed over and adhered to the removable tab such that the secondary sample is deposited on the second sheet during the wipe.

34. The method of claim 26, wherein the at least one sheet comprises one or more sheets for receiving a secondary sample disposed over and adhered to the removable tab, the one or more sheets for receiving a secondary sample configured and arranged such that the secondary sample is deposited thereon during the wipe.

35. The method of claim 26, wherein the step of opening the flap to expose the at least one sheet containing a primary sample comprises peeling the flap via the perforations.

36. The method of claim 26, wherein the secondary test is an immunological test.

37. The method of claim 26, wherein the primary test includes opening the flap and adding a developing solution onto the at least one sheet containing the primary sample.

* * * * *